United States Patent
Jorgenson

(10) Patent No.: US 8,548,584 B2
(45) Date of Patent: Oct. 1, 2013

(54) DEFIBRILLATOR WITH IMPLANTABLE MEDICAL DEVICE DETECTION

(75) Inventor: David J. Jorgenson, Bloomington, MN (US)

(73) Assignee: Physio-Control, Inc., Redmond, WA (US)

( * ) Notice: Subject to any disclaimer, the term of this patent is extended or adjusted under 35 U.S.C. 154(b) by 900 days.

(21) Appl. No.: 12/258,872

(22) Filed: Oct. 27, 2008

(65) Prior Publication Data

US 2009/0054940 A1  Feb. 26, 2009

Related U.S. Application Data

(62) Division of application No. 11/316,198, filed on Dec. 22, 2005, now abandoned.

(51) Int. Cl.
*A61N 1/08* (2006.01)
(52) U.S. Cl.
USPC ........... 607/4; 607/5; 607/10; 607/32; 607/60
(58) Field of Classification Search
USPC ........................................ 607/4, 5, 10, 32, 60
See application file for complete search history.

(56) References Cited

U.S. PATENT DOCUMENTS

| | | | |
|---|---|---|---|
| 4,635,639 A | 1/1987 | Hakala et al. | |
| 5,113,859 A | 5/1992 | Funke | |
| 5,113,869 A | 5/1992 | Nappholz et al. | |
| 5,324,315 A | 6/1994 | Grevious | |
| 5,443,492 A * | 8/1995 | Stokes et al. | 607/131 |
| 5,549,115 A | 8/1996 | Morgan et al. | |
| 5,549,659 A | 8/1996 | Johansen et al. | |
| 5,593,426 A | 1/1997 | Morgan et al. | |
| 5,674,252 A | 10/1997 | Morgan et al. | |

(Continued)

FOREIGN PATENT DOCUMENTS

| | | |
|---|---|---|
| DE | 103 23 627 A1 | 12/2004 |
| WO | WO 02/060529 A2 | 8/2002 |
| WO | WO 2006/083785 A | 8/2006 |

OTHER PUBLICATIONS

"Heartstream FR2 Semi Automatic External Defibrillator (AED)", (5 pgs). http://www.shopmash.com/mash_heartstream_info.htm (last printed Jul. 15, 2003).

(Continued)

*Primary Examiner* — Christopher D Koharski
*Assistant Examiner* — Natasha Patel
(74) *Attorney, Agent, or Firm* — Marger Johnson & McCollom PC

(57) ABSTRACT

In general, the invention is directed to techniques for using an external defibrillator to detect a presence of an implantable medical device (IMD) implanted within a patient, and providing therapy to the patient through communication between the external defibrillator and the IMD. An external defibrillator provides prompts to a user of the external defibrillator to determine the presence of an IMD implanted within the patient. For example, the external defibrillator may prompt the user to visually inspect the patient's chest for signs that an IMD was implanted, such as a scar or raised portion of skin near the patient's clavicles. As another example, the external defibrillator may prompt the user to place a detection device on the patient's chest. The detection device may be coupled to the external defibrillator, and may employ a magnet to initiate telemetry by the IMD to detect the presence of the IMD.

16 Claims, 9 Drawing Sheets

(56) References Cited

U.S. PATENT DOCUMENTS

| | | | |
|---|---|---|---|
| 5,680,864 A | 10/1997 | Morgan et al. |
| 5,683,423 A | 11/1997 | Post |
| 5,749,902 A | 5/1998 | Olson et al. |
| 5,749,913 A | 5/1998 | Cole |
| 5,782,878 A | 7/1998 | Morgan et al. |
| 5,787,155 A | 7/1998 | Luna |
| 5,836,993 A | 11/1998 | Cole |
| 5,891,046 A | 4/1999 | Cyrus et al. |
| 5,891,049 A | 4/1999 | Cyrus et al. |
| 5,899,866 A | 5/1999 | Cyrus et al. |
| 5,921,938 A | 7/1999 | Aoyama et al. |
| 5,951,485 A | 9/1999 | Cyrus et al. |
| 5,999,493 A | 12/1999 | Olson |
| 6,041,257 A | 3/2000 | MacDuff et al. |
| 6,047,207 A | 4/2000 | MacDuff et al. |
| 6,057,758 A | 5/2000 | Dempsey et al. |
| 6,090,056 A | 7/2000 | Bystrom et al. |
| 6,141,584 A | 10/2000 | Rockwell et al. |
| 6,141,588 A | 10/2000 | Cox et al. |
| 6,150,951 A | 11/2000 | Olejniczak |
| 6,201,992 B1 | 3/2001 | Freeman |
| 6,292,698 B1 | 9/2001 | Duffin et al. |
| 6,301,502 B1 | 10/2001 | Owen et al. |
| 6,304,780 B1 | 10/2001 | Owen et al. |
| 6,321,113 B1 | 11/2001 | Parker et al. |
| 6,374,138 B1 | 4/2002 | Owen et al. |
| 6,405,083 B1 | 6/2002 | Rockwell et al. |
| 6,427,083 B1 | 7/2002 | Owen et al. |
| 6,438,417 B1 | 8/2002 | Rockwell et al. |
| 6,477,424 B1 | 11/2002 | Thompson et al. |
| 6,493,581 B2 | 12/2002 | Russell |
| 6,574,511 B2 | 6/2003 | Lee |
| 6,594,634 B1 | 7/2003 | Hampton et al. |
| 6,597,948 B1 | 7/2003 | Rockwell et al. |
| 6,647,299 B2 | 11/2003 | Bourget |
| 6,668,192 B1 | 12/2003 | Parker et al. |
| 6,892,092 B2 | 5/2005 | Palreddy et al. |
| 6,909,916 B2 | 6/2005 | Spinelli et al. |
| 7,167,755 B2 | 1/2007 | Seeberger et al. |
| 7,231,258 B2 * | 6/2007 | Moore et al. .................... 607/60 |
| 2002/0123778 A1 | 9/2002 | Linberg |
| 2002/0169584 A1 | 11/2002 | Fu et al. |
| 2002/0193846 A1 | 12/2002 | Pool et al. |
| 2002/0193848 A1 * | 12/2002 | Lyster et al. .................... 607/62 |
| 2003/0025602 A1 | 2/2003 | Medema et al. |
| 2003/0055458 A1 | 3/2003 | Hamilton et al. |
| 2003/0058097 A1 | 3/2003 | Saltzstein et al. |
| 2003/0109904 A1 | 6/2003 | Silver et al. |
| 2004/0088027 A1 | 5/2004 | Burnes et al. |
| 2004/0127774 A1 | 7/2004 | Moore et al. |
| 2004/0133242 A1 * | 7/2004 | Chapman et al. ................ 607/5 |
| 2004/0138648 A1 | 7/2004 | Sweeny et al. |
| 2004/0199212 A1 | 10/2004 | Fischell et al. |
| 2004/0204744 A1 | 10/2004 | Penner et al. |
| 2004/0225337 A1 | 11/2004 | Housworth et al. |
| 2008/0004663 A1 | 1/2008 | Jorgenson |

OTHER PUBLICATIONS

"ZOLL Software Information". ( 6 pgs). http://www.pinpointtech.com/zolldata/ (last printed Aug. 14, 2002).

"Medium Access Control (MAC) and Physical (PHY) Specifications", ANSI/IEEE Std 802.11, 1999 Edition, (pp. 3-27).

Jaap C. Haartsen et al., "The Bluetooth Radio System" *IEEE Personal Communications*, (pp. 28-26), (Feb. 2000).

Robert F. Bonvini et al., "Pacemaker Spikes Misleading the Diagnosis of Ventricular Fibrillation," Resuscitation 66, pp. 241-243, Jan. 2005.

U.S. Appl. No. 11/047,483, entitled "Communication Between and External Defibrillator and an Implantable Medical Device," filed Jan. 31, 2005.

U.S. Appl. No. 10/330,808, entitled "Communicating Medical Event Information," filed Dec. 26, 2002.

International Search Report PCT/US2006/062483, Intl. filing date Dec. 21, 2005.

"ECC Guidelinges", part 4, The Automatic External Defibrillator, p. 10, "Implanted Pacemakers/ICD" http://circ.ahajournals.org/cgi/content/full/102/suppl_1/I-60.

Resuscitation, Oct. 1995, vol. 30, No. 2, pp. 127-131, ISN 0300-9572 Monsieurs K G et al., "Semi-Automatic External Defibrillation and Implanted Cardiac Pacemakers".

* cited by examiner

US 8,548,584 B2

DEFIBRILLATOR WITH IMPLANTABLE MEDICAL DEVICE DETECTION

This application is a Divisional of U.S. patent application Ser. No. 11/316,198, filed Dec. 22, 2005, the entire content of which is incorporated herein by reference.

TECHNICAL FIELD

The invention relates to emergency medical devices and, more particularly, to external defibrillators.

BACKGROUND

An external defibrillator delivers energy to a heart of a patient via electrodes placed upon the patient's chest. External defibrillators are used to deliver energy in the form of a defibrillation shock to a heart that is undergoing ventricular fibrillation and has lost its ability to contract. Ventricular fibrillation is particularly life threatening because activity within the ventricles of the heart is so uncoordinated that virtually no pumping of blood takes place. If untreated, a patient suffering from fibrillation may die within a matter of minutes.

An electric shock delivered to a fibrillating heart may depolarize the heart and cause it to reestablish a normal sinus rhythm. In some cases, the patient may need multiple shocks, and the external defibrillator may deliver different quantities of energy with each defibrillation shock. Further, the defibrillator may provide additional or alternative therapies to the patient, such as cardioversion or pacing therapy. As examples, the external defibrillator may be an automated external defibrillator (AED) used by a first responder or bystander to treat the patient, or a more fully-featured defibrillator/monitor used by paramedics.

SUMMARY

In general, the invention is directed to an external defibrillator equipped to aid a user in detecting the presence of an implantable medical device (IMD) within a patient. Upon detection of an IMD, the external defibrillator may communicate with the IMD to obtain useful information or coordinate delivery of therapy to the patient. As examples, the external defibrillator may receive patient or therapy information from the IMD, prompt a user based on information received from the IMD, deliver therapy based on information received from the IMD, control delivery of therapy by the IMD, and store information within the IMD. Alternatively, or additionally, detection of IMD location may permit the user to place defibrillation electrodes in a location which will reduce the chance of damage to the IMD while still providing effective defibrillation therapy to the patient.

The external defibrillator may provide prompts to guide a user of the external defibrillator in detecting the presence of an IMD implanted within the patient. For example, the external defibrillator may prompt the user to visually inspect the patient's chest for signs that an IMD was implanted, such as a scar or raised portion of skin near the patient's clavicles. As another example, the external defibrillator may prompt the user to place a detection device on the patient's chest. The detection device may be coupled to the external defibrillator, and may employ a detector to locate an IMD. When an IMD is detected, the external defibrillator or detection device may emit a notification. For example, the detection device may have an audible or visual indicator that assists the user in positioning the detection device.

The external defibrillator may obtain information from a detected IMD or coordinate delivery of therapy with the IMD by wireless telemetry. For example, the detection device may be integrated with wireless telemetry circuitry to facilitate communication with the IMD. In some embodiments, the detection device may include an adhesive interface to permit adhesive fixation of the detection device at the IMD location, thereby promoting more reliable telemetry. The external defibrillator may deliver therapy based on information received from the IMD in the patient. The external defibrillator may select an energy level for a defibrillation shock to be delivered to the patient based on an energy level of a defibrillation shock previously delivered to the patient by the IMD. As another example, the external defibrillator may analyze an electrogram (EGM) or electrocardiogram (ECG), or output received from the IMD indicating pace, shock or sense events, to determine whether to deliver a defibrillation shock to the patient.

In one embodiment, the invention provides an external defibrillator comprising a defibrillation therapy generator, electrodes coupled to the defibrillation therapy generator, and a user interface that presents one or more prompts to a user of the external defibrillator to detect presence of an implantable medical device (IMD) in a patient.

In another embodiment, the invention provides a method comprising generating one or more prompts to a user of an external defibrillator to detect presence of an implantable medical device (IMD) in a patient.

In an additional embodiment, the invention provides an external defibrillator comprising a defibrillation therapy generator, electrodes coupled to the defibrillation therapy generator, and a detection device that detects presence of an implantable medical device (IMD) in a patient.

In another embodiment, the invention provides a method comprising detecting presence of an implantable medical device (IMD) in a patient via a detection device associated with an external defibrillator, and indicating presence of the IMD to a user of the external defibrillator.

In various embodiments, the invention may provide one or more advantages. For example, prompts delivered by an external defibrillator may permit a user to more readily detect the presence and location of an IMD. Upon detection of the IMD location, a user can place defibrillation electrodes at a location which will reduce the chance of damage to the IMD while still providing effective defibrillation therapy to the patient. In addition, a detection device may facilitate rapid detection of the IMD, which promotes timely delivery of therapy. With the ability to communicate with a detected IMD, an external defibrillator may provide more effective treatment to a patient in which the IMD is implanted, permitting coordinated delivery of therapy. In addition, by communication with the IMD, the external defibrillator may more effectively obtain and manage medical information such as patient information or therapy information.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
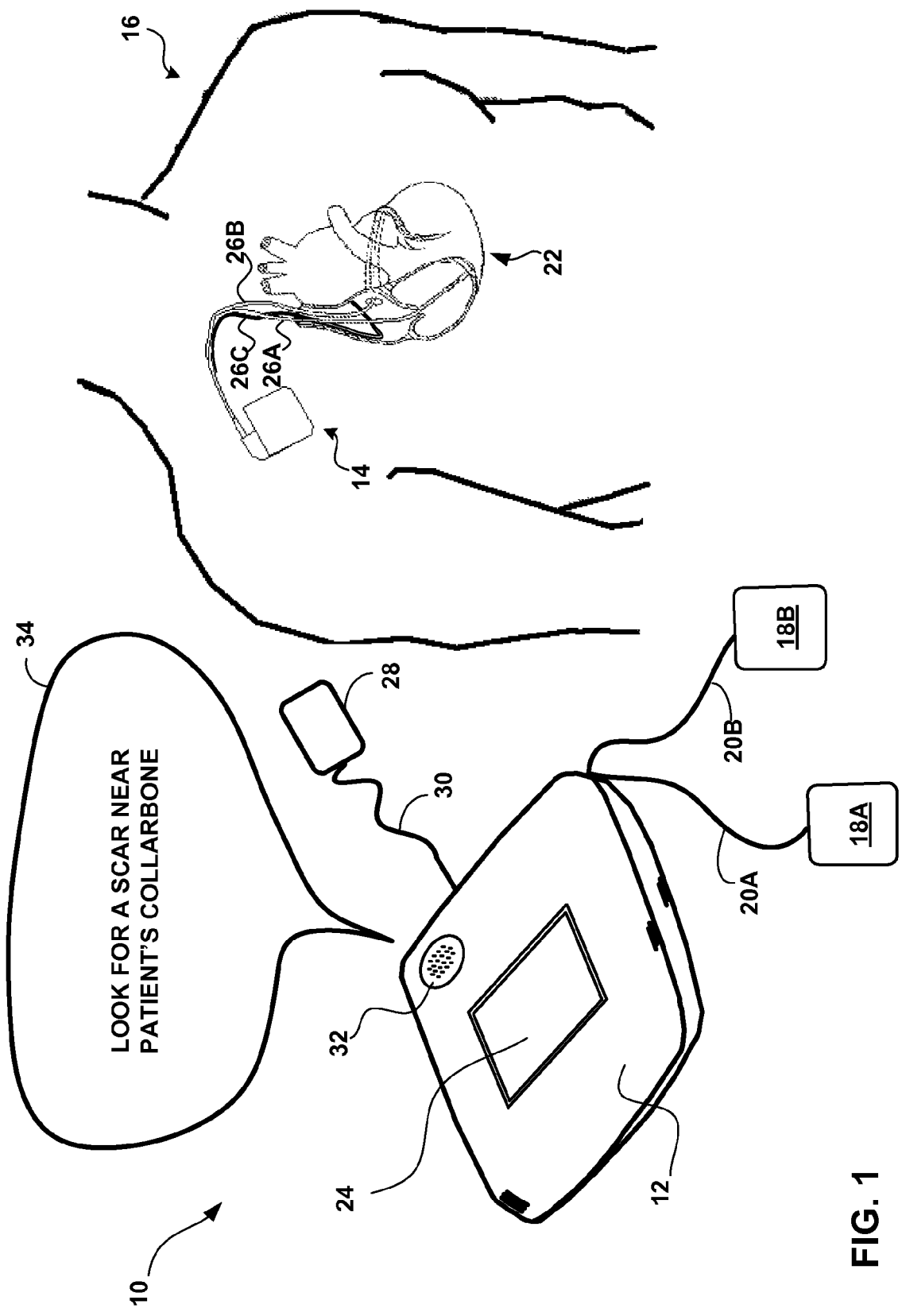
FIG. 1 is a conceptual diagram illustrating an external defibrillator providing a user prompt for locating an IMD implanted within a patient.

FIG. 1 is a conceptual diagram illustrating an example system 10 that includes an external defibrillator 12 providing a user prompt 34 for locating an implantable medical device 14 implanted within a patient 16. External defibrillator 12 may be brought to patient 16 in response to a medical emergency involving patient 16, such as a ventricular fibrillation (VF) or sudden cardiac arrest (SCA) experienced by the patient. External defibrillator 12 may be, for example, an automated external defibrillator (AED), or a more fully featured external defibrillator/monitor, such as those used by paramedics or other medical professional. However, the generation of user prompts may be especially useful to a user of an AED. An AED provides basic life support (BLS) services. A more fully featured external defibrillator/monitor may provide advanced life support (ALS) services.

In the illustrated example, external defibrillator 12 is coupled to two electrodes 18A and 18B (collectively "electrodes 18") that are applied to the skin of patient 16. Electrodes 18 may be electrodes pads, which may include an adhesive backing for attachment to the skin of patient 16, as is known in the art. Electrodes 18 are coupled to defibrillator 12 by respective leads or cables 20A and 20B (collectively "cables 20"). Although illustrated in FIG. 1 as coupled to two electrodes 18, external defibrillator 12 may be coupled to any number of electrodes 18, which may be incorporated into common electrode pads, and may share common cables 20. External defibrillator 12 may additionally include one or more sensors (not shown in FIG. 1), such as blood oxygen saturation or noninvasive blood pressure sensors.

External defibrillator 12 detects electrical activity of the heart 22 of patient 16 via electrodes 18, and delivers electrical stimulation to heart 22 via electrodes 18. For example, defibrillator 12 may deliver one or more defibrillation shocks to patient 16 via electrodes 18. As shown in FIG. 1, defibrillator 12 may include a display 24, and may provide instructions in the form of visual prompts and other information to a user via the display. External defibrillator 12 may, for example, display an electrocardiogram generated based on the electrical activity detected by electrodes 18 via display 24. In some embodiments, as mentioned above, defibrillator 12 may be coupled to additional sensors for sensing other physiological parameters of patient 16, such as blood pressure and oxygen saturation, and may display current or average values for the additional parameters via display 24. External defibrillator 12 may also include a speaker 32 to provide audible user prompts.

In the illustrated example, IMD 14 is a multi-chamber cardiac pacemaker coupled to leads 26A-26C (collectively "leads 26") that extend to selected positions within heart 22, such as the right atrium, right ventricle, and left ventricle. As an alternative or in addition to pacing pulses, IMD 14 may deliver cardioversion and/or defibrillation shocks to heart 22 via leads 26. Hence, IMD 14 may be an implantable cardioverter-defibrillator (ICD), as is known in the art. Further, IMD 14 may sense electrical activity of heart 22 via leads 26.

Leads 26 may include any of a variety of types of electrodes (not shown) known in the art for use in sensing cardiac electrical activity and delivering these types of stimulation to heart 22. The number and positions of leads 26 depicted in FIG. 1 are merely exemplary. Further, the invention is not limited to systems 10 in which an IMD is a pacemaker. IMD 14 may be any type of IMD that senses one or more physiological parameters of patient 16 and/or delivers one or more therapies to the patient. For example, IMD 14 may be an implantable neurostimulator, muscle stimulator, gastrointestinal stimulator, an implantable pump, or an implantable monitor such as an implantable loop recorder.

In the example of FIG. 1, external defibrillator 12 provides a user prompt 34 to aid a user in locating an IMD implanted within patient 16. User prompt 34 may be an audible prompt provided via speaker 32. Alternatively, user prompt 34 may be a visual prompt such as a text prompt, pictorial prompt, or other visual prompt. In some embodiments, defibrillator 12 may provide both audible and visual prompts. External defibrillator 12 may prompt the user to visually inspect an area of the patient's body, e.g., the patient's chest or abdomen for signs that an IMD was implanted in patient 16. Where the patient is a child, an IMD may be implanted in the patient's abdomen. User prompt 34 prompts a user to look for a scar near the patient's clavicle, i.e., collarbone. Such a scar may indicate the presence of an IMD implanted within patient 16. Visual and audible prompts may originate from external defibrillator 12 or from a detection device 28, as will be described, in order to facilitate optimal positioning of the detection device over the patient.

External defibrillator 12 may include a user interface that provides a medium for user input indicating whether the user has found a scar near the patient's clavicle. As one example, display 24 may include interactive touchscreen displays in which the user may push a button shown on display 24 to indicate responses to user prompts. Other interface media such as buttons, switches, hardkeys and softkeys may be used. Such interface media may additionally or alternatively be located on detection device 28. In the case that the user indicates he or she has found a scar near the patient's clavicle, external defibrillator 12 may provide follow-up prompts instructing the user to place detection device 28 on the patient's chest near the scar, so that detection device 28 may establish communication with IMD 14, as described in further detail below.

In some embodiments, external defibrillator 12 is capable of communicating with IMD 14 by wireless telemetry. External defibrillator 12 communicates with IMD 14 via telemetry circuitry similar to that used by dedicated programming devices to communicate with the IMD. Dedicated programming devices may communicate with IMD 14 via its telemetry circuitry to program or reprogram the operating parameters of the IMD, or to retrieve information stored or collected by the IMD, as is known in the art. Like dedicated programming devices, external defibrillator 12 may include corresponding telemetry circuitry to facilitate communication with IMD 14 via its telemetry circuitry. The telemetry circuitry of external defibrillator 12 and IMD 14 may include suitable transceivers, magnets and antennas for communication via radio-frequency (RF) telemetry.

In the example illustrated by FIG. 1, external defibrillator 12 is coupled to detection device 28 by cable 30. Cable 30 may include conductors to carry both power and data to and from detection device 28. Alternatively, in some embodiments, detection device 28 may be battery-powered and communicate with external defibrillator 12 by wireless telemetry. Detection device 28 is placed proximate to, e.g., over, IMD 14 by a user of defibrillator 12 to enable the external defibrillator 12 to detect and optionally communicate with the IMD. In addition to detecting the presence of IMD 14 in patient 16, the detection device 28 may identify or indicate a location of IMD 14 within the patient. In some embodiments, detection device 28 also includes a telemetry device having an antenna and magnet, enabling defibrillator 12 to communicate with the IMD. Defibrillator 12 may be removably or permanently coupled to detection device 28 by cable 30. In some embodiments, detection device 28 may be integral with a housing of external defibrillator 12, or incorporated into one of electrodes 18 and coupled to the external defibrillator by a lead 20. In other embodiments, detection device 28 may not be coupled to defibrillator 12 via cable 30, but may instead communicate with defibrillator 12 via wireless communication, such as RF or infrared communication.

Detection device 28 may include a magnet to open or close a switch within IMD 14 and thereby initiate telemetry by the IMD. In particular, by swiping detection device 28 across the patient's body near a suspected implant site, the detection device triggers wireless telemetry by IMD 14. Telemetry circuitry within detection device 28 then may communicate with IMD 14 and/or measure signal strength of telemetry signals transmitted by IMD 14 to guide the user to place the detection device over the implant site of the IMD. Visual and auditory prompts to guide placement of detection device 28 to a position in proximity to the implant site may originate from the detection device 28 or external defibrillator 12.

For example, detection device 28 may include a visual indicator such as a series of lights. As detection device 28 approaches the implant site of IMD 14, a greater number of lights are activated, thereby guiding placement of the detection device toward the implant site. Alternatively, or additionally, an audible indicator may be provided by detection device 28 or defibrillator 12. For example, the audible indicator may be a speaker that emits an audible beep or pitch that increases in volume or frequency as the detection device 28 approaches the implant site, or speech output much like the prompts described above. The speaker may be provided in detection device 28 or defibrillator 12. In each case, the output of the visual or audible indicator is a function of the measured signal strength of the telemetry signals emitted by IMD 14.

In another embodiment, detection device 28 detects the presence of IMD 14 by inducing IMD 14 to initiate a specific pacing protocol when the magnet is positioned near IMD 14. The frequency and duration of the pacing may be measured by external defibrillator 12 via electrodes 18. Magnet rate profiles are different for different pacemaker and defibrillator manufacturers. The change in pacing rate from before and after detection device 28 was applied would be interpreted by external defibrillator 12 as an IMD. This information may allow external defibrillator 12 to confirm when pacing was occurring and determine whether the patient was in ventricular fibrillation and in need of therapy In some embodiments, the telemetry circuitry and antennae of external defibrillator 12 and IMD 14 may be configured to support a signal strength, other signal characteristics, and communication protocol that allow RF telemetry communication between the external defibrillator and the IMD at relatively greater distances. In such embodiments, one or more antennae of external defibrillator 12 may be housed within the defibrillator. In this case, external defibrillator 12 need not be coupled to detection device 28 to communicate with the IMD, and defibrillator 12 may detect and communicate with IMD when brought into general proximity with the IMD.

Figure 2:
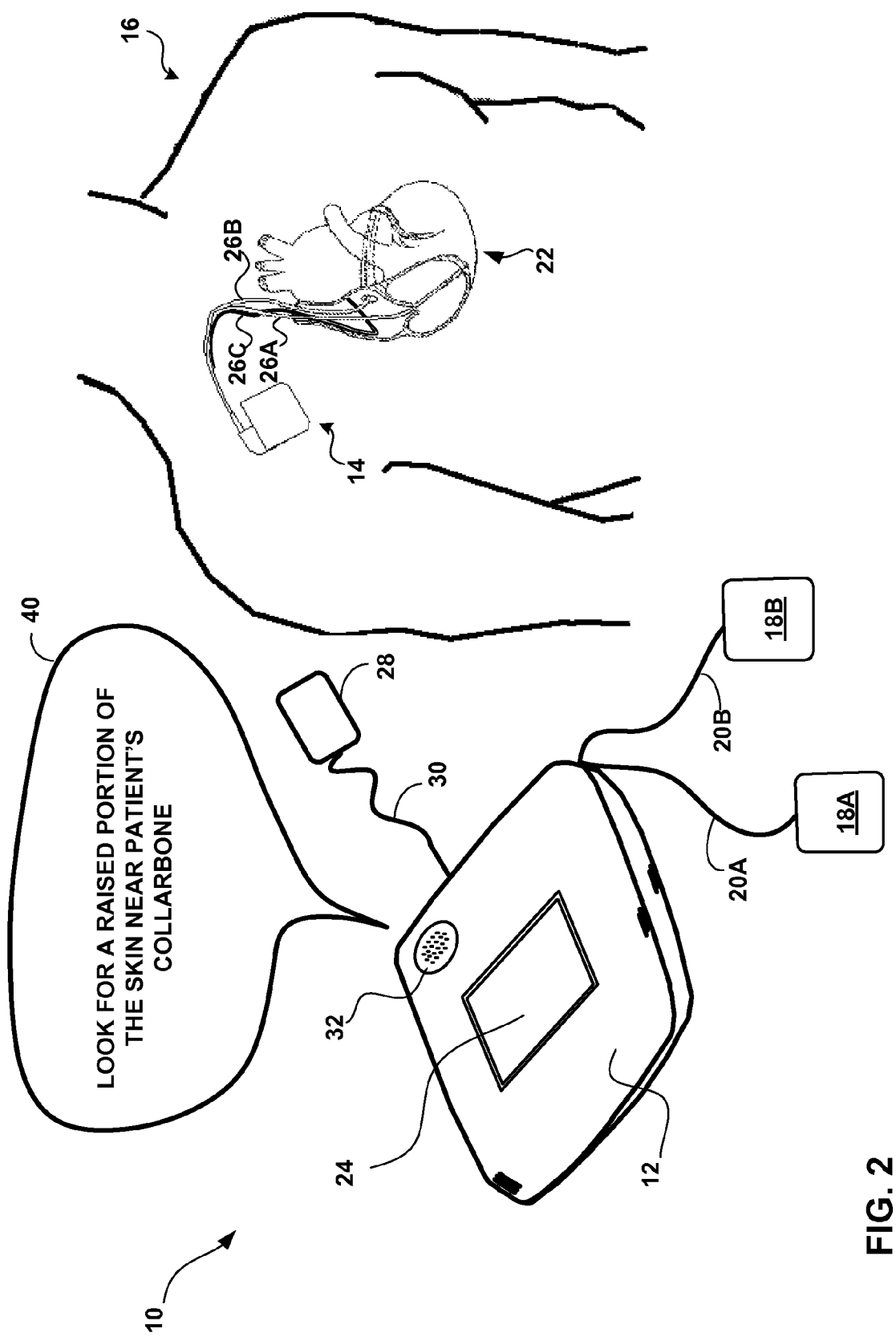
FIG. 2 is a conceptual diagram illustrating an external defibrillator providing a second user prompt for locating an IMD implanted within a patient.

FIG. 2 is a conceptual diagram illustrating external defibrillator 12 in the course of providing another user prompt 40 to aid a user in locating an IMD 14 implanted within a patient 16. Again, user prompt 40 may be a voice prompt provided via speaker 32, a visual prompt provided by display 24, or a combination of both. In the example of FIG. 2, prompt 40 advises the user to visually inspect the patient's chest for other signs that an IMD has been implanted in patient 16. In particular, user prompt 34 prompts a user to look for a raised portion of the skin near patient's collarbone. Such a raised portion of the skin may indicate the presence of an IMD implanted within patient 16.

Prompt 40 may be provided if the user is unable to identify a scar per prompt 34 of FIG. 1. Alternatively, prompt 40 may be provided even if the user identifies a scar in order to aid the user in more precisely identifying the position of IMD 14, which may not be located immediately under the scar. In the case that the user indicates he has found a scar near the patient's clavicle, or found a raised portion of the skin near the patient's collarbone, external defibrillator 12 may provide follow-up voice prompts instructing the user to place detection device 28 on the patient's chest near the scar, so that detection device 28 may verify the presence of IMD 14 and/or establish communication with IMD 14 via telemetry circuitry contained in detection device 28.

External defibrillator 12 may provide other voice prompts to guide the user in determining whether an IMD is implanted within patient 16. For example, external defibrillator 12 may prompt the user to make a tactile search for an IMD by palpitating the patient's chest at an area near the patient's clavicles to feel for an IMD. In other words, the user manipulates the tissue near the clavicles for tactile detection of the IMD, which should feel like a hard object embedded within the tissue. As one example, tactile detection may be done when the patient's size or weight is such that an IMD is not readily visually detectable.

Figure 3:
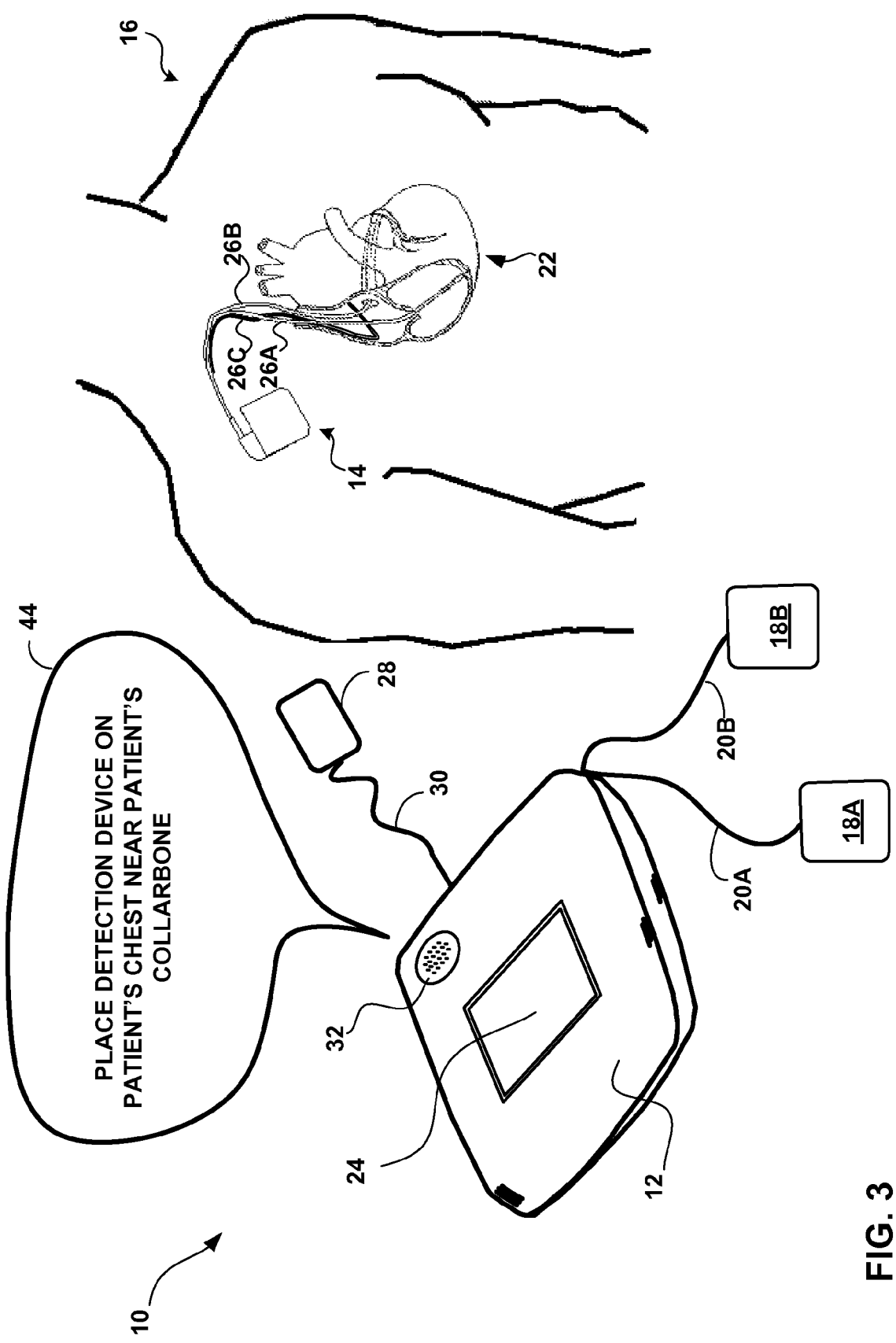
FIG. 3 is a conceptual diagram illustrating an external defibrillator providing a third user prompt for locating an IMD implanted within a patient.

FIG. 3 is a conceptual diagram illustrating external defibrillator 12 in the course of providing another user prompt 44 for locating an implantable medical device 14 implanted within a patient 16. As one example, where a user has been prompted according to FIGS. 1 and 2, but has been unable to visually locate evidence of an IMD in patient 16, external defibrillator 12 may prompt the user via user prompt 44 to place the detection device 28 near an area of the patient's body, e.g., the patient's chest near the patient's clavicle, or the patient's abdomen where the patient is a child.

Detection device 28 may use a magnetic, metal-detecting feature to detect an IMD implanted within patient 16 in a manner similar to a conventional magnetic stud finder. Alternatively, detection device 28 may use another detection method such as an acoustically-based detection method. Consequently, when the user places detection device 28 on the patient's chest near a clavicle, detection device 28 may detect the presence of an IMD implanted within patient 16.

Detection device 28 may contain an output medium that indicates to the user that the detection device has located an IMD, such as LED lights, beeping, text alerts, or other indication means. As another example, display 24 of external defibrillator 12 may display a message indicating that detection device 28 has located an IMD. External defibrillator 12 may display a pictorial indication of a location of IMD 14 within patient 16. Further, detection device 28 may include telemetry circuitry for communicating with IMD 14. In this embodiment, external defibrillator 12 may display a message to indicate that external defibrillator 12 has established communication with IMD 14.

Figure 4:
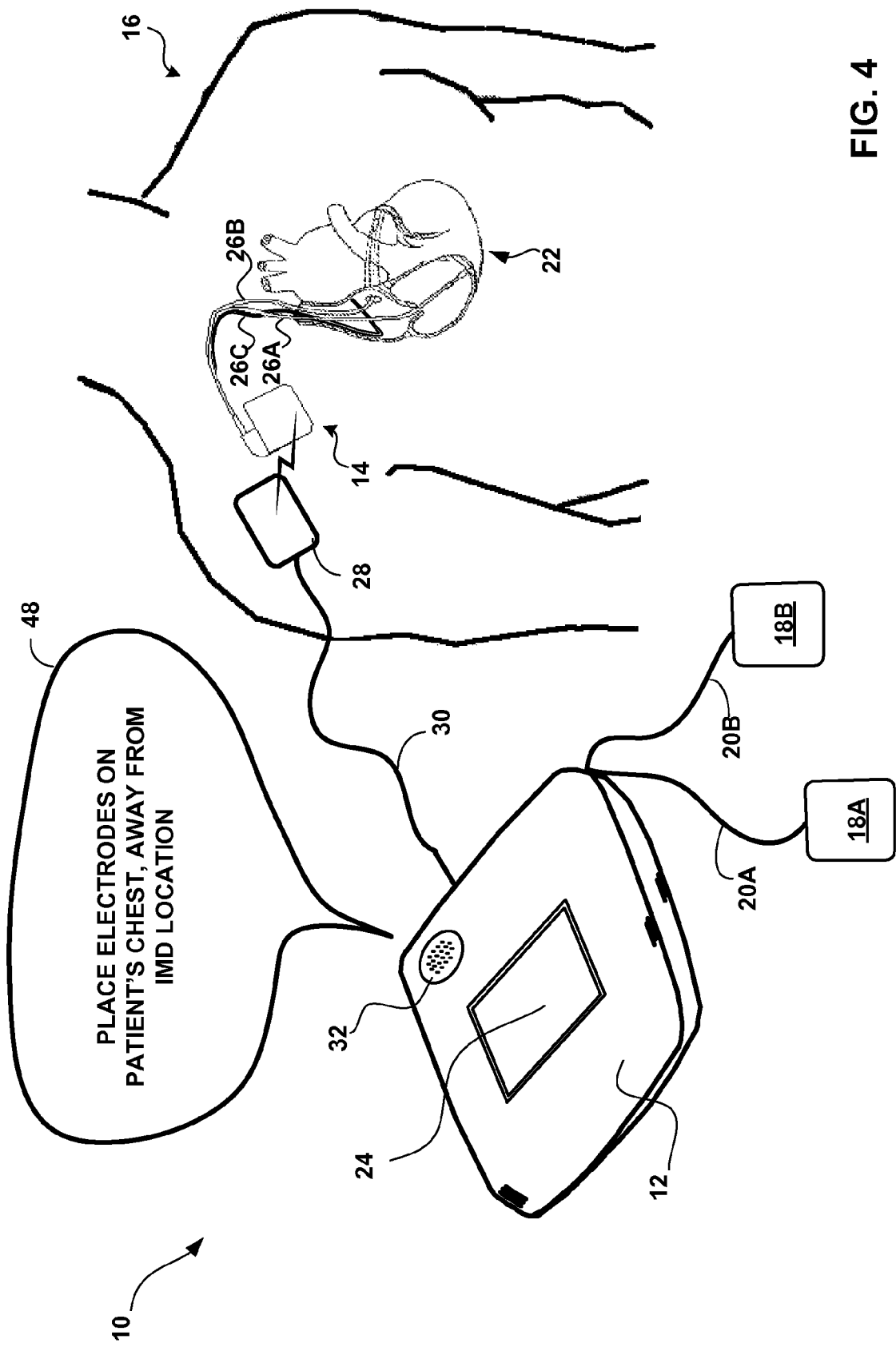
FIG. 4 is a conceptual diagram illustrating an external defibrillator providing a user prompt for placing defibrillation electrodes on a patient.

FIG. 4 is a conceptual diagram illustrating an example system 10 that includes an external defibrillator 12 providing a user prompt 48 for placing electrodes 18 of the external defibrillator 12 on a patient 16. As illustrated in FIG. 4, detection device 28 has been placed on the chest of patient 16, and is in communication with IMD 14. It may be undesirable for external defibrillator electrodes to be placed directly over IMD 14, because energy from electrodes 18 may electrically damage IMD 14. Consequently, external defibrillator 12 prompts a user via user prompt 48 to place the electrodes on the patient's chest, away from the location of the IMD 14. By placing electrodes 18 at locations some distance from the implant location of IMD 14, interference between external defibrillator 12 and IMD 14 may be reduced. Interference between external defibrillator 12 and IMD 14 may include electromagnetic interference, which may degrade the signals generated by sensors of IMD 14 and sensors of external defibrillator 12.

Figure 5:
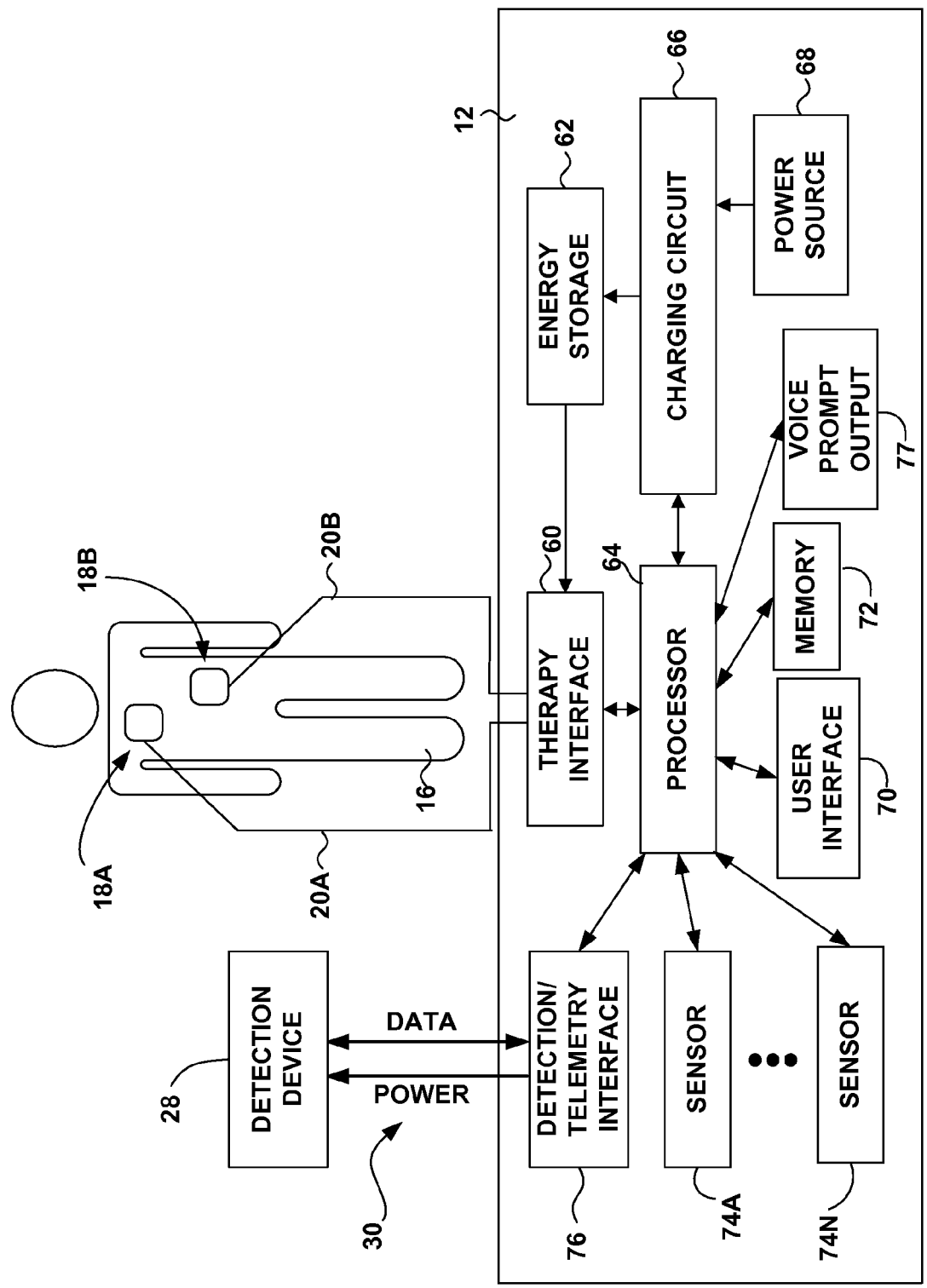
FIG. 5 is a block diagram illustrating example components of the external defibrillator of FIG. 1.

FIG. 5 is a block diagram further illustrating exemplary components of external defibrillator 12. In FIG. 5, external defibrillator 12 is shown coupled to patient 16 by electrodes 18 and corresponding cables 20, as described above. In a typical application, therapy interface 60 of external defibrillator 12 includes a receptacle, and cables 20 plug into the receptacle.

Therapy interface 60 includes a switch (not shown in FIG. 5) that, when activated, couples an energy storage circuit 62 to electrodes 18. Energy storage circuit 62 stores energy to be delivered to patient 16 in the form of a defibrillation shock. The switch may be of conventional design and may be formed, for example, of electrically operated relays. Alternatively, the switch may comprise an arrangement of solid-state devices such as silicon-controlled rectifiers or insulated gate bipolar transistors.

Energy storage circuit 62 includes components, such as one or more capacitors, that store the energy to be delivered to patient 16 via electrodes 18. Before a defibrillation shock may be delivered to patient 16, energy storage circuit 62 must be charged. A processor 64 directs a charging circuit 66 to charge energy storage circuit 62 to a high voltage level. Charging circuit 66 comprises, for example, a flyback charger that transfers energy from a power source 68 to energy storage circuit 62.

As indicated above, external defibrillator 12 may be a manual defibrillator or an AED. Where external defibrillator 12 is a manual defibrillator, a user of defibrillator 12 may select an energy level for each defibrillation shock delivered to patient 16. Processor 64 may receive the selection made by the user via a user interface 70, which may include input devices, such as a keypad and various buttons or dials, and output devices, such as various indicator lights, display 24 (FIG. 1), and a speaker. Display 24 may include a cathode ray tube (CRT), light emitting diode (LED) array, plasma screen, or liquid crystal display (LCD) screen.

Where external defibrillator 12 is an AED, processor 64 selects an energy level. For example, processor 64 may select an energy level from a preprogrammed progression of energy levels stored in a memory 72 based on the number of defibrillation shocks already delivered to patient 16. In some manual defibrillator embodiments, processor 64 may select an energy level, e.g., based on a preprogrammed progression, to recommend to a user via user interface 70.

In either case, when the energy stored in energy storage circuit 62 reaches the desired energy level, processor 64 controls user interface 70 to provide an indication to the user that external defibrillator 12 is ready to deliver a defibrillation shock to patient 16. For example, the indication may be an indicator light or other visual or audible prompt. The defibrillation shock may be delivered manually or automatically. Where the defibrillation shock is delivered manually, the user may direct processor 64 to deliver the defibrillation shock via user interface 70 by, for example, pressing a button. In either case, processor 64 activates the switches of interface 60 to electrically connect energy storage circuit 62 to electrodes 18, and thereby deliver the defibrillation shock to patient 16. Therapy interface 60, energy storage circuitry 62 and charging circuit 66 are examples of therapy delivery circuitry that deliver therapy to patient 16 under control of processor 64.

Processor 64 or other circuitry modulates the defibrillation shock waveform delivered to patient 16. Processor 64 may, for example, control the switches of interface 60 to regulate the shape and width of the shock. Processor 64 may control the switches to modulate the shock to, for example, provide a multiphasic shock, such as a biphasic truncated exponential shock, as is known in the art.

Processor 64 may perform other functions as well, such as monitoring electrical activity of the heart of patient 16 sensed via electrodes 18. Therapy interface 60 may include circuitry for sensing the electrical activity of the heart via electrodes 18. Processor 64 determines whether heart 22 of patient 16 is fibrillating based upon the sensed electrical activity in order to determine whether a defibrillation shock should be delivered to patient 16. Where a defibrillation shock has already been delivered, processor 64 evaluates the efficacy of the delivered defibrillation shock by determining if heart 22 is still fibrillating in order to determine whether an additional defibrillation shock is warranted. Processor 64 may automatically deliver defibrillation shocks based on these determinations, or may advise the caregiver of these determinations via user interface 70. Processor 64 may display an electrocardiogram (ECG) that reflects the sensed electrical activity via user interface 70, e.g., via display 24 (FIG. 1).

Processor 64 may store an indication of the time of delivery of each defibrillation shock delivered to patient 16 as medical event information within memory 72 for patient 16. Processor 64 may also store the energy level of each pulse and other characteristics of each pulse, such as the width, amplitude, or shape, as medical event information for patient 16. Processor 64 may also store a digital representation of the ECG, or a heart rate over time determined based on the electrical activity of the heart of patient 16 detected via electrodes 18 within memory 72 as medical event information for patient 16. Further, processor 64 may control delivery of other types of therapy to patient 16 via electrodes 18, such as cardioversion or pacing therapy, and store information describing the times that such therapies were delivered and parameters of such therapies, such as cardioversion pulse energy levels and pacing rates, as medical event information for patient 16.

Where external defibrillator 12 is more fully featured, e.g., a manual paramedic or hospital defibrillator, defibrillator 12 may also include additional sensors 74A-74N (collectively "sensors 74") coupled to processor 64, such as sensors to measure blood oxygen saturation, blood pressure, respiration, and the amount of oxygen or carbon dioxide in the air inhaled or exhaled by patient 16. Sensors 74 may be included within or coupled to external defibrillator 12. External defibrillator 12 may include circuitry that conditions the signals generated by sensors 74 such that they may be analyzed by processor 64, such as one or more analog to digital converters to, and suitable filter and amplifier circuitry.

Processor 64 may also store the signals generated by these sensors within memory 72 as medical event information for patient 16. As examples, processor 64 may store any of a capnograph, a plethysmograph, a blood oxygen saturation over time, a blood pressure over time, a pulse rate over time determined based on measured blood pressure, end tidal carbon dioxide measurements, and/or measurements of the fraction of carbon dioxide in air inspired or expired within memory 72 as medical event information for patient 16. Processor 64 may also receive other information collected by a user during treatment of patient 16, such as a location of treatment or time of death, and store such information as medical event information for the patient. Processor 64 may begin to store medical event information in memory 72 when defibrillator 12 is powered on to respond to a medical emergency involving patient 16.

Processor 64 may, for example, include one or more of a microprocessor, DSP, ASIC, FPGA, or other equivalent integrated or discrete logic circuitry. Memory 72 may include program instructions that cause processor 64 to perform the functions attributed to processor 64 and defibrillator 12 herein. Accordingly, this disclosure also contemplates computer-readable media storing instructions to cause processor 64 to provide the functionality described herein. Memory 72 may include any of a variety of solid state, magnetic or optical media, such as RAM, ROM, CD-ROM, magnetic disk, EEPROM, or flash memory.

In the example illustrated by FIG. 5, external defibrillator 12 includes a detection/telemetry interface 76. Detection/telemetry interface 76 may include a port or other physical interface to receive cable 30, which is coupled to detection device 28, and to electrically couple circuitry within defibrillator 12 to circuitry within detection device 28 via cable 30. Cable 30 may include conductors to carry both power and data to and from detection device 28. Alternatively, detection device 28 may be battery-powered and communicate with external defibrillator 12 by wireless telemetry. Processor 64 communicates with IMD 14 via detection/telemetry interface 76 and detection device 28.

In some embodiments, as illustrated in FIG. 5, detection/telemetry interface 76 may convey data between processor 64 and detection device 28, as well as provide power from defibrillator 12 to power the circuitry within detection device 28. As will be described below with reference to FIG. 7, detection device 28 may incorporate wireless telemetry circuitry and one or more antennae for communication with IMD 14. Detection device 28 may also incorporate a magnet to trigger initiation of telemetry by IMD 14. In such embodiments, detection/telemetry interface 76 may include any of a variety of known digital data interfaces, such as a universal serial bus (USB) interface. In some embodiments, the detection device may not be integrated with telemetry circuitry. In such embodiments, detection device 28 may be configured simply to trigger initiation of telemetry by IMD 14. Telemetry circuitry may be incorporated within defibrillator 12, or there may be a separate telemetry interface and telemetry head, independent of detection device 28, for providing communication with IMD 14.

In other embodiments, external defibrillator 12 may include the telemetry circuitry, and detection device 28 may include only one or more antennae for communication with IMD 14. In this case, detection device 28 receives wireless telemetry signals from IMD 14 but transmits the received signals to defibrillator for processing. Further, in still other embodiments, defibrillator 12 may include both telemetry circuitry and antennae for communication with IMD 14. Defibrillator 12 need not be coupled to detection device 28 in order to communicate with IMD 14. In such embodiments, detection device 28 may provide wireless communication with defibrillator 12, and may be battery powered, e.g., with a non-rechargeable or rechargeable battery, instead of receiving power from defibrillator 12.

Figure 6:
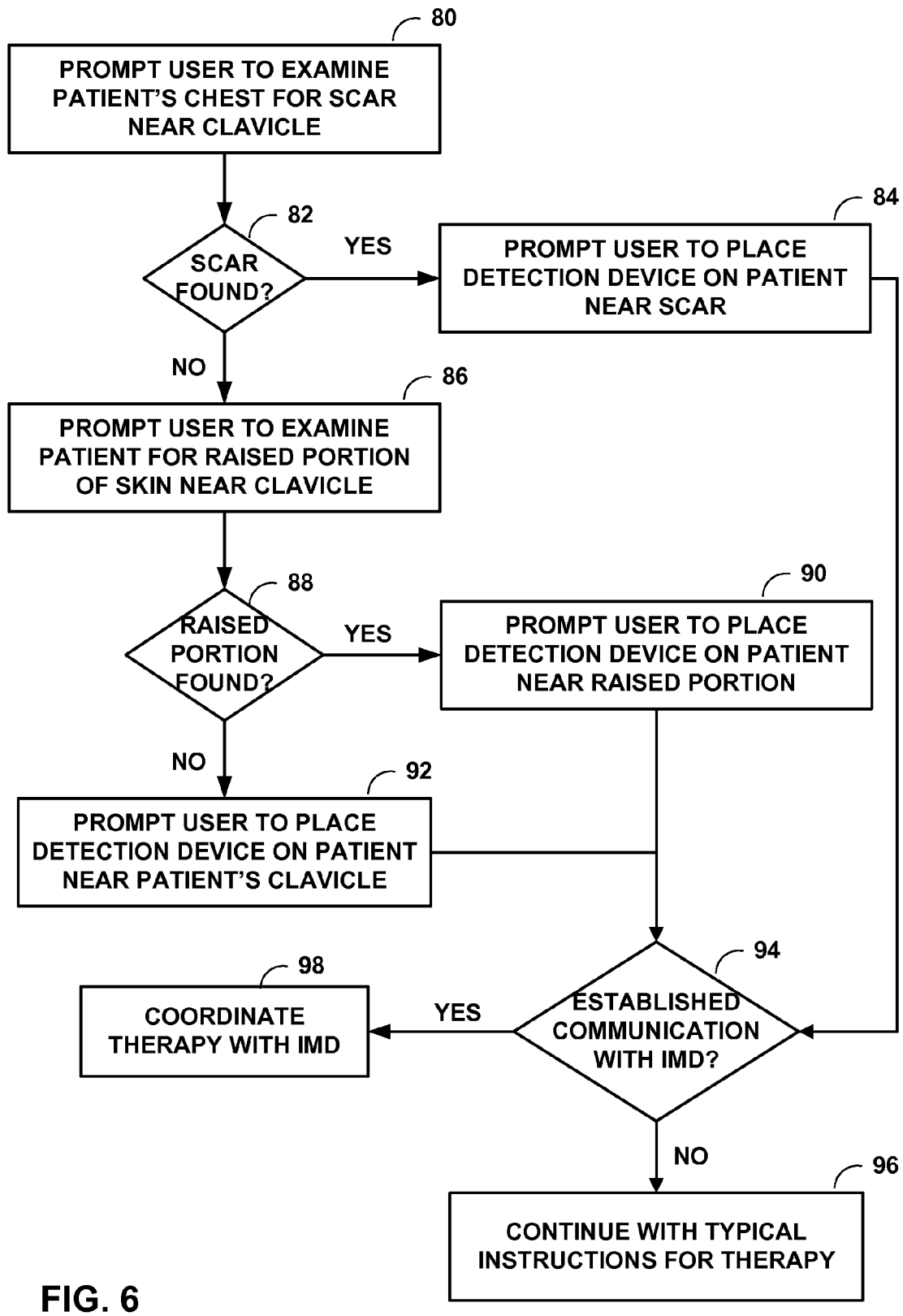
FIG. 6 is a flowchart illustrating exemplary operation of an external defibrillator.

FIG. 6 is a flowchart illustrating exemplary operation of external defibrillator 12. External defibrillator 12 is brought to patient 16 in response to a medical emergency involving patient 16, such as a ventricular fibrillation (VF) or sudden cardiac arrest (SCA) experienced by the patient. A user operates external defibrillator 12, and follows prompts from external defibrillator 12 to visually inspect patient 16 to determine whether patient 16 has an IMD, and if so, to determine the location of the IMD within patient 16. In some embodiments, the user is aided not only by visual or audible prompts, but also detection device 28.

In the example of FIG. 6, external defibrillator 12 prompts the user to examine the patient's chest for a scar near the patient's clavicle (80). As mentioned previously, external defibrillator 12 may include a user interface that provides a medium for user input indicating whether the user has found a scar near the patient's clavicle. If the user indicates he has found such a scar (yes branch of 82), external defibrillator 12 prompts the user to place detection device 28 on the patient near the scar (84), so that detection device 28 may initiate communication by IMD 14, e.g., by triggering telemetry with a magnet carried by detection device 28.

If the user indicates he does not find such a scar (no branch of 82), external defibrillator 12 prompts the user to examine the patient for a raised portion of skin near the patient's clavicle (86). If the user indicates he has found such a raised portion of skin (yes branch of 88), external defibrillator 12 prompts the user to place detection device 28 on the patient near the raised portion (90), so that detection device 28 may initiate communication by IMD 14. Again, detection device 28 may integrate wireless telemetry circuitry for communication with IMD 14, or simply include a magnet to trigger telemetry by IMD 14.

If the user indicates he does not find such a raised portion of skin (no branch of 88), external defibrillator 12 prompts the user to place detection device 28 on the patient near the patient's clavicle (92). External defibrillator 12 may provide other prompts (not shown) prompting the user to move the detection device to various areas of the patient's chest to use the detection capabilities of the detection device to search for an IMD. For example, the user may swipe detection device 28 across the patient's chest, near the clavicle or elsewhere, to initiate telemetry by IMD 14. Detection device 28 may include telemetry circuitry to detect telemetry signals, and thereby detect the presence of IMD 14. Based on detected signal strength, detection device 28 may indicate the relative proximity of the detection device 28 to the implant site of IMD 14. As discussed previously, detection device 28 may include a visible or audible indicator, or both, to indicate the strength of the telemetry signal, and hence the distance from the IMD 14. An indicator, such as an array of lights in which more lights are lit as signal strength becomes stronger, can help the user guide detection device 28 toward the implant site of IMD 14. In turn, upon placement of detection device 28 in close proximity to IMD 14, the increased strength of the telemetry signal will promote more reliable telemetry with the IMD.

In embodiments in which detection device 28 includes telemetry circuitry for communicating with IMD 14, detection device 28 placed on the patient's chest may attempt to establish communication with IMD 14 (94). If communication cannot be established, external defibrillator 12 may continue with its typical therapy instructions without communicating with an IMD (98). As one example, detection device 28 may be unable to establish communication because patient 16 does not have an IMD at all. As another example, detection device 28 may be unable to locate an IMD implanted within patient 16. If communication is established with IMD 14, then external defibrillator 12 may coordinate therapy with IMD 14 (98), as described in further detail below.

Figure 7:
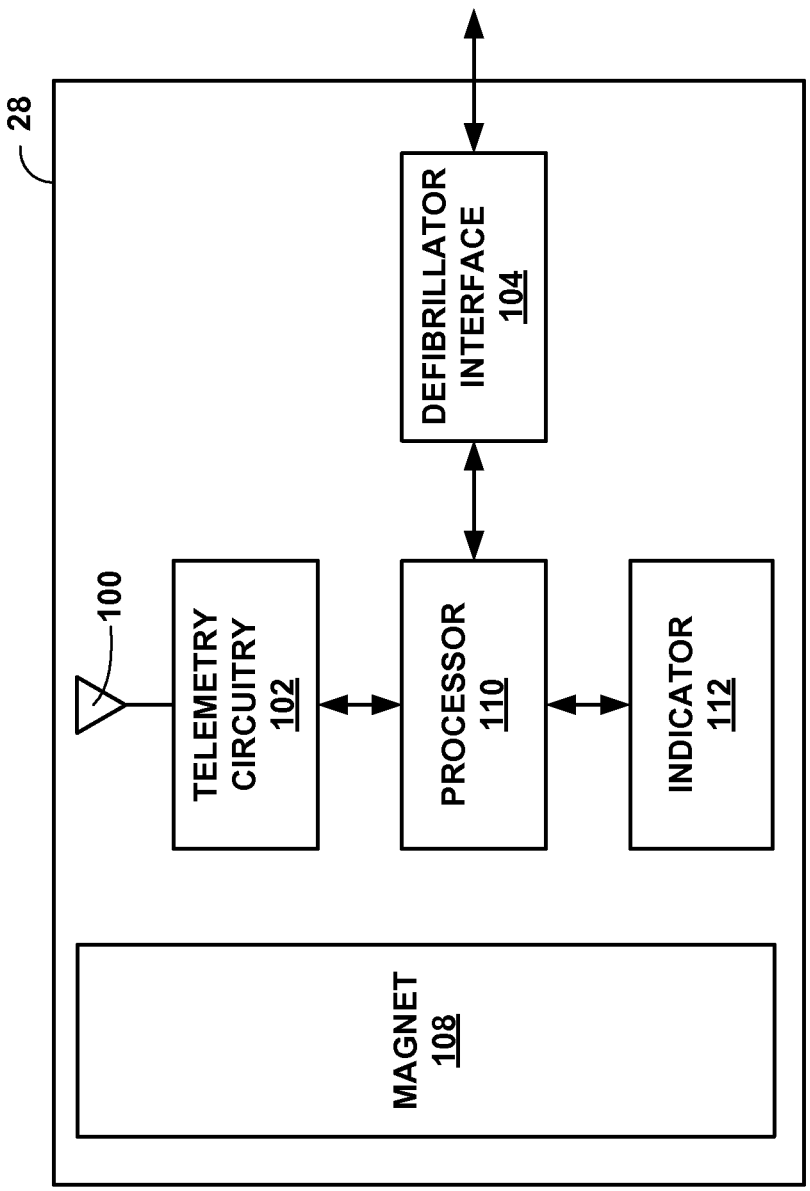
FIG. 7 is a block diagram illustrating example components of an IMD detection device for use with the external defibrillator of FIG. 1.

FIG. 7 is a block diagram further illustrating an exemplary detection device 28 of FIG. 1. In the illustrated example, detection device 28 includes an antenna 100 coupled to telemetry circuitry 102. Telemetry circuitry 102 includes a wireless transceiver for RF communication with IMD 14 via antenna 100. Telemetry circuitry 102 may also include various circuitry for conditioning signals transmitted or received via antenna 100, such as analog to digital and digital to analog converters, and appropriate amplifiers or filters.

A defibrillator interface 104 of detection device 28 interfaces with detection/telemetry interface 76 (FIG. 5) of external defibrillator 12. Interface 104 may include a plug or other physical interface on cable 30 that may be used to removably or permanently couple detection device 28 to defibrillator 12, and which electrically couples the circuitry within detection device 28 to circuitry within defibrillator 12 via detection/telemetry interface 76. As illustrated in FIG. 7, interface 104 may convey data between telemetry circuitry 102 and external defibrillator 12, and may receive power from defibrillator 12 for distribution to the various components of detection device 28. Interface 104 may include any of a variety of known digital data interfaces, such as a universal serial bus (USB) connector. In some embodiments, the USB interface also may carry operating power for components of detection device 28. In other embodiments, interface 104 may communicate with defibrillator 12 via a wireless interface, such as an RF or infrared interface. In these embodiments, defibrillator 12 need not be coupled to detection device 28 in order to communicate with IMD 14. In such embodiments, detection device 28 may be battery powered instead of receiving power from defibrillator 12.

Detection device 28 also includes a magnet 108 to trigger initiation of telemetry by IMD 14 when detection device 28 is swiped across the patient's body in proximity to the IMD implant site. Processor 110 processes signals received from telemetry circuitry 102, e.g., for transmission to defibrillator 12 via defibrillator interface 104. In addition, processor 110 may measure the signal strength of telemetry signals received via telemetry circuit 102 in order to drive an indicator 112, such as a visual or audible indicator. As described above, indicator serves to indicate the relative proximity of detection device 28 to IMD 14 based on the measured signal strength of telemetry signals received from the IMD. The signal strength measurement may be performed for digital signals converted by telemetry circuitry 102. Alternatively, an analog signals strength measurement may be obtained by an analog measurement circuit based on analog signals received by telemetry circuitry. In either case, the signal strength measurement is used to drive indicator 112.

Figure 8:
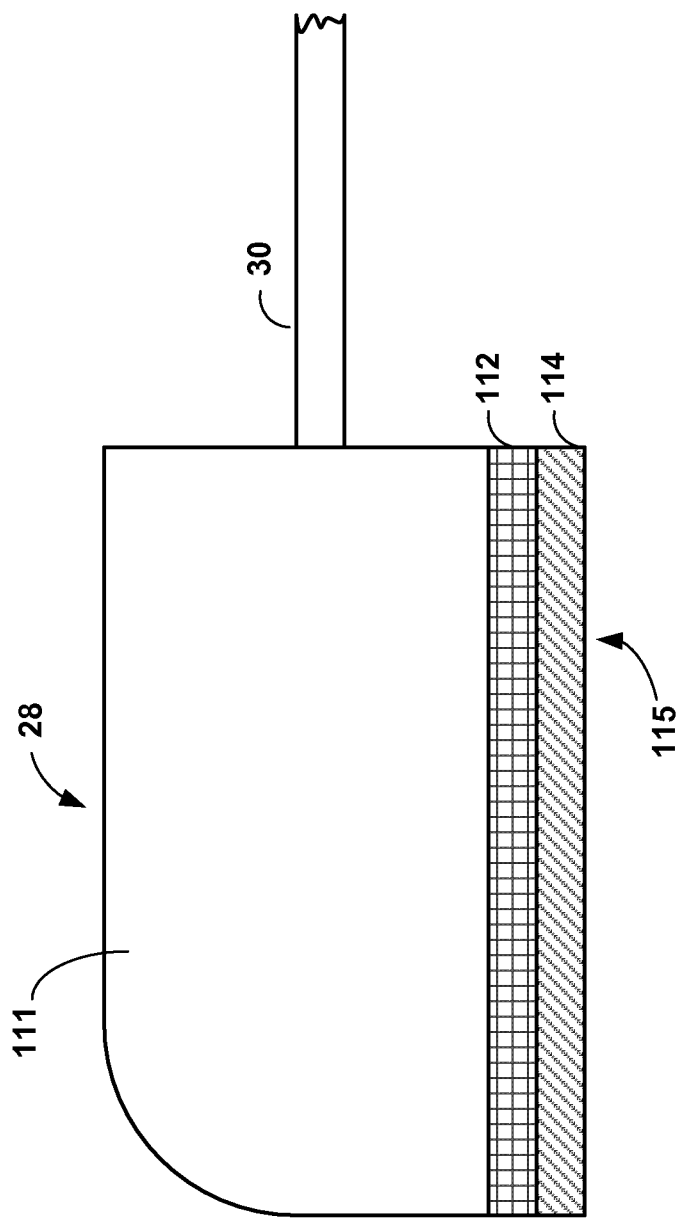
FIG. 8 is a block diagram illustrating an example IMD detection device that includes an adhesive layer and a removable backing layer.

FIG. 8 is a block diagram illustrating an example detection device 28. In the example of FIG. 8, detection device 28 includes a housing 111, an adhesive layer 112 and a removable backing strip 114. Detection device 28 is coupled to external defibrillator 12 by cable 30. Adhesive layer 112 may comprise a layer of non-toxic adhesive for adhering detection device 28 to the skin of patient 16. A user may remove removable backing layer 114 to expose adhesive layer 112, and then attach detection device 28 to patient 16. In operation, a bottom surface 115 of detection device 28 has a substantially planar surface designed to engage and slide across the skin of patient 16.

In one embodiment, once a location of IMD 14 within patient 16 has been determined, defibrillator 12 may prompt the user to attach detection device 28 to the patient's skin over IMD 14. In particular, the user removes backing layer 114 to expose adhesive layer 112, and thereby permit adhesive fixation of detection device 28 to the skin of patient 16 at the location of the IMD. In this manner, when detection device 28 includes telemetry circuitry, detection device 28 remains in proximity to IMD 14 to maintain communication between the two devices, even when patient 16 is moved or transported. Adhesive layer 114 thereby promotes reliable and robust communication between defibrillator 12 and IMD 14. In one embodiment, detection device 28 may be a disposable unit that may be decoupled from cable 30 or defibrillator 12 and discarded after use.

Figure 9:
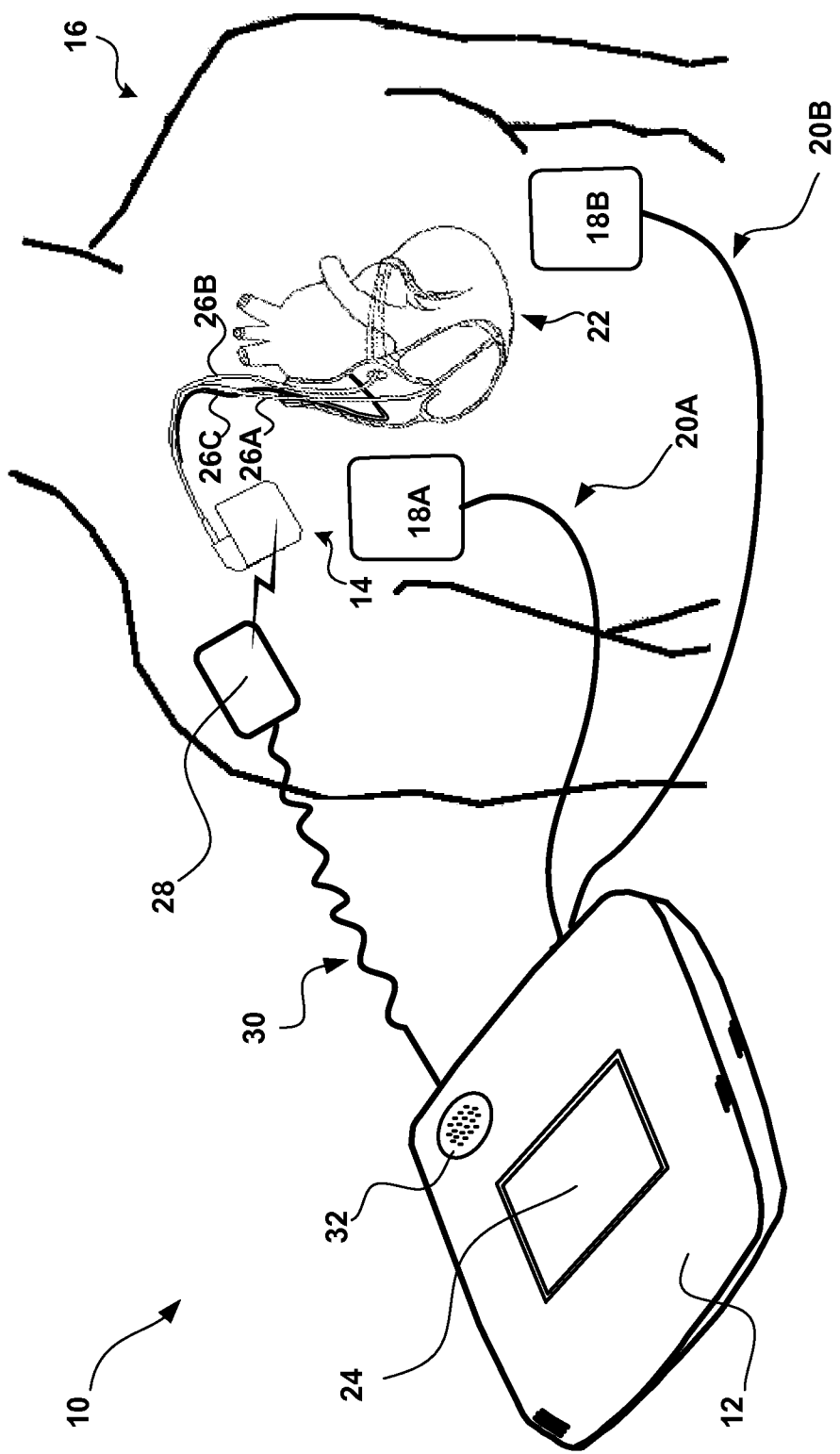
FIG. 9 is a conceptual diagram illustrating an example system that includes an external defibrillator communicating with an IMD implanted within a patient.

FIG. 9 is a conceptual diagram illustrating an example system 10 that includes an external defibrillator 12 communicating with an IMD 14 implanted within a patient 16, e.g., via detection device 28 or independently of detection device 28. IMD 14 may store a variety of information regarding patient 16 and IMD 14 itself within a memory unit of IMD 14 (not shown), and external defibrillator 12 may retrieve this information from IMD 14 during a telemetry session. For example, IMD 14 may store demographic information for patient 16, such as name, height, weight, sex, age, residence, date of birth, and the like. Further, IMD 14 may store treatment alerts for patient 16, such as medications taken by the patient, allergies of the patient, physician name, physician phone number, patient's hospital, patient history, patient medical condition, patient blood type, or a do not resuscitate (DNR) order for the patient.

IMD 14 may store information describing the type of IMD 14, pacemaker or internal defibrillator lead types, ejection fraction, implant lead data, an implant date, lead configuration, lead impedance and current programmed parameters, such as a current pacing mode, pacing amplitude, or defibrillation amplitude. IMD 14 may also store information identifying the implant location of IMD 14. When processor 64 of external defibrillator 12 receives such information from IMD 14, processor 64 may store the information in memory 72 as medical event information for patient 16. Such information may then be included in a report of the treatment of patient 16, e.g., a "run" report, along with other medical event information collected by external defibrillator 12 as discussed above with reference to FIG. 5. Alternatively, such information may be received directly by a run reporting system from IMD 14. Paramedics, first responders, or other users of external defibrillator 12 may be required to prepare such run reports by an emergency medical service or other regulating authority. Alternatively, or additionally, such information may be downloaded from the detection device or the run reporting system to a database management system of an emergency room or other location. The information would then be available to a physician.

Because external defibrillator 12 may retrieve such patient and device information from IMD 14 and include the information within the medical event information for patient 16 automatically, a user of the external defibrillator may not be required to take time to collect such information from patient 16, family members, or bystanders, and enter the information into external defibrillator 12 manually via user interface 70 of the defibrillator. Consequently, the user's time and attention may remain focused on treating patient 16. In some embodiments, if external defibrillator 12 is an AED, it may be configured to transfer such information to another defibrillator, such as an ALS defibrillator carried by a paramedic, e.g., by wired or wireless communication, or by physical transfer of a memory card or other data storage medium.

IMD 14 may also store physiological and therapy information. For example, IMD 14 may store information relating to current status and history of therapy delivery by the IMD to patient 16. External defibrillator 12 may retrieve this stored information from IMD 14, and may also receive real-time values for one or more physiological parameters and real-time indications of therapies delivered or scheduled for delivery by the IMD from the IMD. For example, external defibrillator 12 may receive EGM samples sensed by IMD 14 via leads 26, and may receive a real-time ECG recorded and stored by IMD 14. EGM signals are a record of changes of cardiac electric potentials, as measured with electrodes placed within the heart, either through catheters or transvenous leads. Real-time ECG samples may be collected using electrodes built into the IMD exterior metal housing. External defibrillator 12 may store any or all of the past or real-time information received from IMD 14 within memory 72.

In addition, external defibrillator 12 may receive information indicating events or operations within an implanted device, such as pacing, shock or sensing events, all of which may be referred to as IMD event information. An example of such information is the information presented by the Marker Channel™ functionality provided by various IMDs manufactured by Medtronic, Inc. of Minneapolis, Minn. Such IMD event information can be used by the external defibrillator 12 to interpret operation of IMD 14. For instance, if the patient is in ventricular fibrillation, a life threatening event, and the patient has a pacemaker that is delivering pacing pulses, external defibrillator 12 may use the IMD event information obtained from IMD 14 to determine if the pulses it records from the electrodes 18 are occurring at the same time as the paced events indicated by the IMD event information. If so, then external defibrillator 12 can conclude that the IMD 14 is generating these events. As another example, external defibrillator 12 may use electrodes 18 to measure the rate of change of a measured voltage to recognize pacing pulses. In either case, the external defibrillator 12 can then analyze periods between the pacing pulses to identify ventricular fibrillation or send a command to the pacemaker to change the pacing rate to facilitate better interpretation of the patient's intrinsic rhythm. As a further example, external defibrillator 12 may detect an impedance signal generated by IMD 14, e.g., changes in tissue impedance due to pacing pulses by IMD 14. External defibrillator 12 may use this information to determine that IMD 14 is present within patient 16.

Further, external defibrillator 12 may receive EGM or heart rate data stored by IMD 14, or ECG information obtained via electrodes 18, including average values or other statistical summaries of the heart rate of patient 16 over time. External defibrillator 12 may also receive current heart rate values, or current average heart rate value, e.g., averaged over a relatively short period of time such as a minute, from the IMD. External defibrillator 12 may also receive stored or real-time values for other physiological parameters that may be detected by IMD 14 as discussed above, such as blood pressure and blood flow. Using this information, external defibrillator 12 can make more informed shock decisions, and control the timing and parameters of shocks delivered to the patient by the external defibrillator.

Processor 64 of external defibrillator 12 may provide prompts to a user via user interface 70, e.g., via speaker 32 and/or display 24, based on the information received from IMD 14. In some embodiments, providing prompts based on the information received from IMD 14 comprises modifying programmed prompts that may have otherwise been provided to a user of defibrillator 12 in the absence of communication with IMD 14. For example, memory 72 of external defibrillator 12 may store visual or audible prompts provided to a user by processor 64 that indicate locations for the user to place electrodes 18 on patient 16. If an IMD 14 is detected, however, the prompts may be modified to direct the user to place electrodes 18 at locations situated at a distance from the IMD implant site. For example, the prompts may advise the user to place the defibrillation electrodes 18 at least six inches (15.24 cm) away from the IMD implant site. In this manner, electromagnetic interference between external defibrillator 12 and IMD 14, as well as risk of damage to or reprogramming of IMD 14 caused by defibrillation shock energy levels, may be reduced. Positioning the electrodes 18 further away from the IMD 14 may be beneficial to improve the performance of the IMD and external defibrillator 12 when both are present and operating together.

As another example, processor 64 may prompt a user of external defibrillator 12 with patient treatment alert information received from IMD 14. For example, processor 64 may provide prompts to the user indicating allergies, potential drug interactions, patient history, patient medical condition, or a DNR order for patient 16. Because patient treatment alert information may impact treatment decisions made by a user of external defibrillator 12, processor 64 may use bold or flashing text, flashing lights, audible alerts, or the like to draw the attention of the user to the presence of one or more patient treatment alerts.

Additionally, processor 64 may prompt a user with a time of onset of the current medical emergency, or a time elapsed since onset of the medical emergency, based on the time of onset information received from IMD 14. The efficacy of therapies that could be delivered to the patient may vary based on the amount of time elapsed since onset of the medical emergency, e.g., amount of time in fibrillation or SCA. Consequently, a user of external defibrillator 12 may provide different therapies to patient 16 based on the time of onset or amount of time elapsed indicated by external defibrillator 12 based on information received from IMD 14. For example, a user of external defibrillator 12 may elect to deliver defibrillation shocks to patient 16 if the patient has been in SCA or fibrillation for less than five minutes, and elect to perform CPR on the patient if the patient has been in SCA or fibrillation for greater than five minutes. In some embodiments, external defibrillator 12 may prompt the user to provide a particular therapy or type of monitoring based on the onset or elapsed time information received from IMD.

Further, if the received information indicates that IMD 14 is scheduled to deliver a therapy to patient 16, processor 64 may provide a prompt notifying the user of the upcoming delivery of therapy. For example, IMD 14 may identify a shockable arrhythmia of heart 22, and transmit an indication to external defibrillator 12 that IMD 14 will deliver a defibrillation shock to the heart. Processor 64 may direct the user to avoid contact with patient, e.g., stop CPR, for a period of time to avoid receiving a portion of the energy of the defibrillation shock delivered by IMD 14, which may cause discomfort or injury to the user.

Processor 64 may also display some or all of the information received from IMD 14 via display 24. For example, processor 64 may receive and display the name of patient 16 as stored by IMD 14, allowing a user of external defibrillator 12 to address the patient by name without having to ask the patient, family members, or other bystanders.

Further, processor 64 may display real-time values of physiological parameters sensed by IMD 14, such as a real-time ECG or EGM sensed by IMD 14 via leads 26, via display. Through communication with IMD 14, external defibrillator 12 may be able to display values of physiological parameters that may not have otherwise been able to be sensed by external defibrillator 12. Processor 64 may provide prompts based on some of these values. For example, processor 64 may provide audio or visual prompts regarding the efficacy of CPR provided by a user of external defibrillator 12, e.g., instruction to apply more or less forceful chest compressions, based on blood pressure or blood flow values measured by IMD 14.

EGM waveforms detected by IMD 14 via leads 26 or ECG waveforms may be of a higher quality than an ECG detected by external defibrillator 12 via electrodes 18. For example, an EGM or ECG waveform detected by IMD 14 may be less likely to include motion artifacts caused by CPR chest compressions than an ECG detected by the external defibrillator. Consequently, where available from IMD 14, processor 64 of the external defibrillator may display a real-time EGM or ECG waveforms received from IMD 14. In some embodiments, the processor may select either the ECG detected by the external defibrillator or ECG or EGM received from the IMD based on criteria related to the quality of the ECGs, such as noise or impedance. For example, the processor may select the IMD ECG or EGM when available unless signal to noise ratio of the external ECG, i.e., the ECG detected by the external defibrillator, is above a threshold value.

Processor 64 may also display information indicating therapies delivered to patient 16 by IMD 14 via display 22. Processor 64 may also display information indicating a current status of IMD 14, i.e., what IMD 14 is currently doing. If the displayed information indicates that the IMD has already delivered therapy to patient 16 in response to the current medical emergency, the user may consider such information and thereby avoid delivering redundant therapies to patient 16. For example, the displayed information may indicate energy levels of defibrillation shocks delivered to patient by IMD 14, and the user may select an energy level for a defibrillation shock to be delivered by external defibrillator 12 that is adjusted based on the energy levels of the defibrillation shocks delivered by the IMD. For example, the user may select an energy level for a defibrillation shock to be delivered by external defibrillator 12 that is greater than the energy levels of the defibrillation shocks delivered by the IMD if the pulse delivered by the IMD failed to defibrillate heart 22.

External defibrillator 12 may also deliver therapy to patient 16 based on the information received from IMD 14. For example, in embodiments in which processor 64 selects an energy level for a defibrillation shock to be delivered to patient 16 by external defibrillator 12, processor 64 may select the energy level based on the information. The information received from IMD 14 may indicate an energy level of a defibrillation shock delivered to patient 16 by IMD 14, and processor 64 may select an energy level for a defibrillation shock to be delivered by external defibrillator 12 based on the indicated energy level. Processor 64 may select a higher energy level to avoid delivering a redundant defibrillation shock which may have already proven ineffective at ending fibrillation of heart 22.

As another example, in embodiments in which processor 64 analyzes an ECG to determine whether to deliver therapy, e.g., a defibrillation shock, to patient 16, processor 64 may analyze a real-time ECG received from IMD 14. As discussed above, the ECG or EGM received from IMD 14 may be of a higher quality, e.g., less susceptible to motion artifacts from CPR chest compressions, than an ECG detected via electrodes 18. Consequently, by using an ECG or EGM received from IMD 14, processor 64 may be able to more accurately determine whether therapy should be delivered to patient 16. Additionally, as discussed above, processor 64 may select one of the IMD and external ECG for analysis based on a criterion related to the quality of at least one of the ECGs, thereby supporting coordinated operation of external defibrillator 12 and IMD 14.

Further, in some embodiments, IMD 14 may use different algorithms to determine whether to deliver therapy to patient 16 than are available to processor 64, and processor 64 may deliver therapy based on a therapy delivery decision received from IMD 14. For example, IMD 14 may apply arrhythmia detection algorithms to the rhythm of heart 22 that distinguish between ventricular and supra-ventricular arrhythmias. IMD 14 may decide that a defibrillation shock should be delivered in response to detection of a ventricular arrhythmia, and that a defibrillation shock should not be delivered in response to detection of a supra-ventricular arrhythmia. Processor 64 may control delivery of a defibrillation shock to patient 16 based on a defibrillation shock delivery decision received from IMD 14. In this manner, external defibrillator 12 may, for example, avoid delivering a defibrillation shock to treat a supra-ventricular arrhythmia. In some embodiments, a user may override a decision by processor 64 not to deliver therapy based on information received from IMD 14, and direct defibrillator 12 to deliver therapy.

Additionally, processor 64 may control delivery of therapy by external defibrillator 12, e.g., control charging circuit 66 and therapy delivery interface 60, based on onset or elapsed time information received from IMD 14. For example, processor 64 may select a therapy, such as defibrillation, cardioversion or pacing, or the energy levels for such therapy, based on the time. Processor 64 may alternatively suspend delivery of therapy by external defibrillator 12 based on the time information.

Processor 64 of external defibrillator 12 may also control delivery of therapy by IMD 14. For example, processor 64 may suspend delivery of therapy by IMD 14 during treatment of patient 16 with external defibrillator 12. By suspending delivery of therapy by IMD 14, external defibrillator 12 may avoid interference between therapies delivered by IMD 14 and defibrillator 12. As another example, external defibrillator 12 may deliver therapy upon receiving information from IMD 14 that IMD 14 has a low battery, or that IMD 14 has delivered a maximum number of shocks.

As another example, processor 64 may change a therapy delivery mode of IMD 14. For example, after defibrillation by external defibrillator 12, some patients may benefit from pacing in a different mode than the mode in which IMD 14 had been programmed. Processor 64 may change the mode of IMD 14 by, for example, changing IMD 14 from single to dual chamber pacing or from demand to non-demand pacing, or by changing a pacing rate or the aggressiveness of rate responsive pacing or by increasing pacing amplitudes.

Further, the hearts of some patients are left in a state of pulseless electrical activity after being defibrillated. Such patients may benefit from delivery of post extra-systolic potentiation (PESP) pacing, which may increase the cardiac output of their heart. If IMD 14 is capable of delivering post extra-systolic pacing pulses, processor 64 may direct IMD 14 to do so after heart 22 has been defibrillated. In some embodiments, processor 64 may direct IMD 14 to delivery other therapies provided by the IMD that may not be available from the external defibrillator, such as cardioversion or anti-tachycardia pacing therapies or by increasing pacing amplitudes, after the shock was delivered by the AED.

Additionally, processor 64 may direct IMD 14 to deliver therapy that is coordinated with therapy delivered by defibrillator 12. For example, processor 64 may direct IMD 14 to deliver a defibrillation shock synchronized with, or with some other temporal relationship to, a defibrillation shock delivered by defibrillator 12. Delivery of defibrillation shocks by both IMD 14 and external defibrillator 12 may be more efficacious than delivery of defibrillation shocks by either the external defibrillator or the IMD alone.

As another example, external defibrillator 12 may include pacing circuitry for delivery of pacing pulses to heart 22 of patient 16 via electrodes 18. To the extent IMD 14 is not capable of delivering post extra-systolic pacing pulses, processor 64 may control the pacing circuitry to deliver pacing pulses an extra-systolic interval after delivery of a pacing pulse by IMD 14, or an intrinsic depolarization of heart 22. Processor 64 of external defibrillator 12 may interrogate IMD 14 to identify the therapies sensing capabilities provided by the IMD. Processor 64 may control the IMD to deliver a therapy alone, or in coordination with the external defibrillator, based on this capability information retrieved from the IMD.

As described above, processor 64 collects medical event information during treatment of patient 16 with external defibrillator 12, and stores the medical event information within memory 72 of the external defibrillator. Processor 64 may also store the medical event information into IMD 14. In this manner, caregivers who subsequently treat patient 16 and have access to a programming device that communicates with IMD 14 may be able to retrieve the medical event information. In the absence of communication between IMD 14 and external defibrillator 12, such caregivers may not have had access or timely access to the medical event information, which may inform treatment decisions made by the caregivers, and may supplement the medical records maintained for patient 16 by the caregivers. In some embodiments, rather than a caregiver retrieving the information with a programming device, IMD 14 may transmit the medical event information to a computing device, computing network, or other data repository at, for example, a hospital. The medical event information may supplement the hospitals records for the patient, and may be available to caregivers throughout the hospital who may treat the patient.

Various embodiments of the invention have been described. However, one skilled in the art will appreciate that various modifications may be made to the described embodiment without departing from the scope of the claimed invention. For example, although wireless communication has been described herein primarily in the context of RF telemetry, the invention is not so limited. An external defibrillator and IMD according to the invention may include any of a variety of RF, optical, acoustic, or other transducers for wireless communication. Further, although described in the context of communication with an IMD, an external defibrillator according to the invention may communicate with other external medical devices that are associated with the patient, such as a wearable defibrillator or Holter monitor. In addition, although described in the context of an external defibrillator, the IMD may be any implantable device, such as a neurostimulator, a drug pump, or a diabetes monitoring device. These and other embodiments are within the scope of the following claims.

The invention claimed is:

1. An external defibrillator for defibrillating a patient, the external defibrillator comprising:
    a defibrillation therapy generator for use with electrodes that can be attached to skin of the patient; and
    a user interface that presents one or more prompts to a user of the external defibrillator to detect presence of an implantable medical device (IMD) in the patient by requesting that the user examine an area of the body of the patient for evidence of presence of an IMD in the patient.

2. The external defibrillator of claim 1, wherein the user interface presents:
    a first prompt requesting that the user examine a chest of the patient for a scar near clavicles of the patient;
    a second prompt requesting that the user examine the chest of the patient for a raised portion of skin near the clavicles of the patient;
    a third prompt requesting that the user place a detection device on the chest of the patient near the clavicles of the patient; and
    a fourth prompt requesting that the user place the electrodes on the patient's chest based on the location of the IMD.

3. The external defibrillator of claim 1, wherein the prompts include at least one of audible prompts or visual prompts, the external defibrillator including a device to present at least one of the audible prompts or visual prompts.

4. The external defibrillator of claim 1, wherein the user interface provides a medium for user input indicating that the user has detected presence of the IMD.

5. The external defibrillator of claim 1, further comprising a detection device that detects presence of the IMD, wherein the detection device is configured to trigger initiation of telemetry by the IMD and detect the presence of the IMD based on reception of one or more telemetry signals from the IMD.

6. The external defibrillator of claim 5, further comprising a processor that receives information from the IMD via the telemetry signals, wherein the processor controls the therapy generator to deliver therapy to the patient based on the received information.

7. The external defibrillator of claim 6, wherein the received information includes electrogram information, electrocardiogram information, and IMD event information.

8. A method comprising generating one or more prompts to a user of an external defibrillator to detect presence of an implantable medical device (IMD) in a patient.

9. The method of claim 8, further comprising presenting a prompt requesting that9 the user examine an area of the body of the patient for evidence of presence of the IMD in the patient.

10. The method of claim 8, further comprising generating:
    a first prompt requesting that the user examine a chest of the patient for a scar near clavicles of the patient;
    a second prompt requesting that the user examine the chest of the patient for a raised portion of skin near the clavicles of the patient;
    a third prompt requesting that the user place a detection device of the external defibrillator on the chest of the patient near the clavicles of the patient; and
    a fourth prompt requesting that the user place electrodes of the external defibrillator on the patient's chest based on the location of the IMD.

11. The method of claim 8, wherein generating one or more prompts includes generating at least one of audible prompts or visual prompts.

12. The method of claim 8, wherein detecting presence of an IMD in the patient comprises triggering initiation of telemetry by the IMD and detecting the presence of the IMD based on reception of one or more telemetry signals from the IMD.

13. The method of claim 12, further comprising:
   receiving information from the IMD via the telemetry signals; and
   delivering therapy to the patient based on the received information.

14. The method of claim 13, wherein the received information includes electrogram information, electrocardiogram information, and IMD event infonnation.

15. An external defibrillator for defibrillating a patient, the external defibrillator comprising:
   a defibrillation therapy generator for use with electrodes that can be attached to skin of the patient;
   a user interface configured to provide prompts to a user;
   a detection interface for receiving data regarding an implantable medical device (IMD) in the patient; and
   a processor connected to the user interface and detection interface, the processor configured to generate user prompts on the user interface to request that the user examine an area of the body of the patient for evidence of presence of an IMD in the patient.

16. The external defibrillator of claim 15, in which the processor is further configured to end the user prompts on the user interface when the processor receives data from the detection interface indicating the presence of an IMD in the patient.

\* \* \* \* \*